US010226597B2

United States Patent
Millett

(10) Patent No.: US 10,226,597 B2
(45) Date of Patent: Mar. 12, 2019

(54) GUIDEWIRE WITH CENTERING MECHANISM

(71) Applicant: VOLCANO CORPORATION, San Diego, CA (US)

(72) Inventor: Bret Millett, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 889 days.

(21) Appl. No.: 14/201,070

(22) Filed: Mar. 7, 2014

(65) Prior Publication Data
US 2014/0257248 A1  Sep. 11, 2014

Related U.S. Application Data

(60) Provisional application No. 61/774,228, filed on Mar. 7, 2013.

(51) Int. Cl.
| | | |
|---|---|---|
| *A61M 25/09* | (2006.01) | |
| *A61B 8/12* | (2006.01) | |
| *A61M 25/04* | (2006.01) | |
| *A61M 25/10* | (2013.01) | |

(52) U.S. Cl.
CPC ......... *A61M 25/09041* (2013.01); *A61B 8/12* (2013.01); *A61M 25/04* (2013.01); *A61M 2025/1047* (2013.01)

(58) Field of Classification Search
CPC .... A61M 25/09041; A61M 2025/1047; A61M 25/04; A61M 25/104; A61M 25/10; A61M 25/09; A61M 25/0108; A61B 8/12
See application file for complete search history.

(56) References Cited

U.S. PATENT DOCUMENTS

| | | | |
|---|---|---|---|
| 3,301,258 | A | 1/1967 | Werner |
| 3,617,880 | A | 11/1971 | Cormack et al. |
| 3,789,841 | A | 2/1974 | Antoshkiw |
| 3,841,308 | A | 10/1974 | Tate |
| 4,140,364 | A | 2/1979 | Yamashita et al. |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

Sihan et al., 2008, A novel approach to quantitative analysis of intraluminal optical coherence tomography imaging, Comput. Cardiol:1089-1092.

(Continued)

*Primary Examiner* — Brandy S Lee

(57) ABSTRACT

The invention provides a guidewire with a centering mechanism. The mechanism lifts the guidewire from a vessel wall and biases it towards the center of the vessel. Since the guidewire can be selectively lifted away from the vessel wall, scraping the catheter against the wall can be avoided, the tip can be guided into the correct branch of a bifurcation, and an imaging device can be used to its full potential. In certain aspects, the invention provides a guidewire with an elongated shaft with a proximal portion and a distal portion comprising a distal tip. One or more centering mechanism can be provided on a guidewire.

9 Claims, 11 Drawing Sheets

(56) References Cited

U.S. PATENT DOCUMENTS

| | | |
|---|---|---|
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,715,378 A * | 12/1987 | Pope, Jr. ............ A61M 25/104 604/913 |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,979,939 A * | 12/1990 | Shiber .................. A61B 8/12 604/22 |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |

(56) References Cited

U.S. PATENT DOCUMENTS

| | | |
|---|---|---|
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,904,657 A * | 5/1999 | Unsworth ......... A61M 25/0155 600/434 |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |

(56) References Cited

U.S. PATENT DOCUMENTS

| | | | |
|---|---|---|---|
| 6,673,064 B1 | 1/2004 | Rentrop | |
| 6,685,648 B2 | 2/2004 | Flaherty et al. | |
| 6,689,056 B1 | 2/2004 | Kilcoyne et al. | |
| 6,689,119 B1 * | 2/2004 | Di Caprio | A61M 25/0127 600/585 |
| 6,689,144 B2 | 2/2004 | Gerberding | |
| 6,696,173 B1 | 2/2004 | Naundorf et al. | |
| 6,701,044 B2 | 3/2004 | Arbore et al. | |
| 6,701,176 B1 | 3/2004 | Halperin et al. | |
| 6,709,444 B1 | 3/2004 | Makower | |
| 6,712,836 B1 | 3/2004 | Berg et al. | |
| 6,714,703 B2 | 3/2004 | Lee et al. | |
| 6,719,717 B1 | 4/2004 | Johnson et al. | |
| 6,725,073 B1 | 4/2004 | Motamedi et al. | |
| 6,726,677 B1 | 4/2004 | Flaherty et al. | |
| 6,730,107 B2 | 5/2004 | Kelley et al. | |
| 6,733,474 B2 | 5/2004 | Kusleika | |
| 6,738,144 B1 | 5/2004 | Dogariu | |
| 6,740,113 B2 | 5/2004 | Vrba | |
| 6,746,464 B1 | 6/2004 | Makower | |
| 6,780,157 B2 | 8/2004 | Stephens et al. | |
| 6,795,188 B2 | 9/2004 | Ruck et al. | |
| 6,795,196 B2 | 9/2004 | Funakawa | |
| 6,798,522 B2 | 9/2004 | Stolte et al. | |
| 6,822,798 B2 | 11/2004 | Wu et al. | |
| 6,830,559 B2 | 12/2004 | Schock | |
| 6,832,024 B2 | 12/2004 | Gerstenberger et al. | |
| 6,842,639 B1 | 1/2005 | Winston et al. | |
| 6,847,449 B2 | 1/2005 | Bashkansky et al. | |
| 6,855,115 B2 | 2/2005 | Fonseca et al. | |
| 6,856,138 B2 | 2/2005 | Bohley | |
| 6,856,400 B1 | 2/2005 | Froggatt | |
| 6,856,472 B2 | 2/2005 | Herman et al. | |
| 6,860,867 B2 | 3/2005 | Seward et al. | |
| 6,866,670 B2 | 3/2005 | Rabiner et al. | |
| 6,878,113 B2 | 4/2005 | Miwa et al. | |
| 6,886,411 B2 | 5/2005 | Kjellman et al. | |
| 6,891,984 B2 | 5/2005 | Petersen et al. | |
| 6,895,106 B2 | 5/2005 | Wang et al. | |
| 6,898,337 B2 | 5/2005 | Averett et al. | |
| 6,900,897 B2 | 5/2005 | Froggatt | |
| 6,912,051 B2 | 6/2005 | Jensen | |
| 6,916,329 B1 | 7/2005 | Zhao | |
| 6,922,498 B2 | 7/2005 | Shah | |
| 6,937,346 B2 | 8/2005 | Nebendahl et al. | |
| 6,937,696 B1 | 8/2005 | Mostafavi | |
| 6,943,939 B1 | 9/2005 | DiJaili et al. | |
| 6,947,147 B2 | 9/2005 | Motamedi et al. | |
| 6,947,787 B2 | 9/2005 | Webler | |
| 6,949,094 B2 | 9/2005 | Yaron | |
| 6,952,603 B2 | 10/2005 | Gerber et al. | |
| 6,954,737 B2 | 10/2005 | Kalantar et al. | |
| 6,958,042 B2 | 10/2005 | Honda | |
| 6,961,123 B1 | 11/2005 | Wang et al. | |
| 6,966,891 B2 | 11/2005 | Ookubo et al. | |
| 6,969,293 B2 | 11/2005 | Thai | |
| 6,969,395 B2 | 11/2005 | Eskuri | |
| 6,985,234 B2 | 1/2006 | Anderson | |
| 7,004,963 B2 | 2/2006 | Wang et al. | |
| 7,006,231 B2 | 2/2006 | Ostrovsky et al. | |
| 7,010,458 B2 | 3/2006 | Wilt | |
| 7,024,025 B2 | 4/2006 | Sathyanarayana | |
| 7,027,211 B1 | 4/2006 | Ruffa | |
| 7,027,743 B1 | 4/2006 | Tucker et al. | |
| 7,033,347 B2 | 4/2006 | Appling | |
| 7,035,484 B2 | 4/2006 | Silberberg et al. | |
| 7,037,269 B2 | 5/2006 | Nix et al. | |
| 7,042,573 B2 | 5/2006 | Froggatt | |
| 7,044,915 B2 | 5/2006 | White et al. | |
| 7,044,964 B2 | 5/2006 | Jang et al. | |
| 7,048,711 B2 | 5/2006 | Rosenman et al. | |
| 7,049,306 B2 | 5/2006 | Konradi et al. | |
| 7,058,239 B2 | 6/2006 | Singh et al. | |
| 7,060,033 B2 | 6/2006 | White et al. | |
| 7,060,421 B2 | 6/2006 | Naundorf et al. | |
| 7,063,679 B2 | 6/2006 | Maguire et al. | |
| 7,068,852 B2 | 6/2006 | Braica | |
| 7,074,188 B2 | 7/2006 | Nair et al. | |
| 7,095,493 B2 | 8/2006 | Harres | |
| 7,110,119 B2 | 9/2006 | Maestle | |
| 7,113,875 B2 | 9/2006 | Terashima et al. | |
| 7,123,777 B2 | 10/2006 | Rondinelli et al. | |
| 7,130,054 B2 | 10/2006 | Ostrovsky et al. | |
| 7,139,440 B2 | 11/2006 | Rondinelli et al. | |
| 7,153,299 B1 | 12/2006 | Tu et al. | |
| 7,171,078 B2 | 1/2007 | Sasaki et al. | |
| 7,175,597 B2 | 2/2007 | Vince et al. | |
| 7,177,491 B2 | 2/2007 | Dave et al. | |
| 7,190,464 B2 | 3/2007 | Alphonse | |
| 7,215,802 B2 | 5/2007 | Klingensmith et al. | |
| 7,218,811 B2 | 5/2007 | Shigenaga et al. | |
| 7,236,812 B1 | 6/2007 | Ballerstadt et al. | |
| 7,245,125 B2 | 7/2007 | Harer et al. | |
| 7,245,789 B2 | 7/2007 | Bates et al. | |
| 7,249,357 B2 | 7/2007 | Landman et al. | |
| 7,291,146 B2 | 11/2007 | Steinke et al. | |
| 7,292,715 B2 | 11/2007 | Furnish | |
| 7,292,885 B2 | 11/2007 | Scott et al. | |
| 7,294,124 B2 | 11/2007 | Eidenschink | |
| 7,300,460 B2 | 11/2007 | Levine et al. | |
| 7,335,161 B2 | 2/2008 | Von Arx et al. | |
| 7,337,079 B2 | 2/2008 | Park et al. | |
| 7,355,716 B2 | 4/2008 | de Boer et al. | |
| 7,356,367 B2 | 4/2008 | Liang et al. | |
| 7,358,921 B2 | 4/2008 | Snyder et al. | |
| 7,359,062 B2 | 4/2008 | Chen et al. | |
| 7,359,554 B2 | 4/2008 | Klingensmith et al. | |
| 7,363,927 B2 | 4/2008 | Ravikumar | |
| 7,366,376 B2 | 4/2008 | Shishkov et al. | |
| 7,382,949 B2 | 6/2008 | Bouma et al. | |
| 7,387,636 B2 | 6/2008 | Cohn et al. | |
| 7,391,520 B2 | 6/2008 | Zhou et al. | |
| 7,397,935 B2 | 7/2008 | Kimmel et al. | |
| 7,399,095 B2 | 7/2008 | Rondinelli | |
| 7,408,648 B2 | 8/2008 | Kleen et al. | |
| 7,414,779 B2 | 8/2008 | Huber et al. | |
| 7,440,087 B2 | 10/2008 | Froggatt et al. | |
| 7,447,388 B2 | 11/2008 | Bates et al. | |
| 7,449,821 B2 | 11/2008 | Dausch | |
| 7,450,165 B2 | 11/2008 | Ahiska | |
| RE40,608 E | 12/2008 | Glover et al. | |
| 7,458,967 B2 | 12/2008 | Appling et al. | |
| 7,463,362 B2 | 12/2008 | Lasker et al. | |
| 7,463,759 B2 | 12/2008 | Klingensmith et al. | |
| 7,491,226 B2 | 2/2009 | Palmaz et al. | |
| 7,515,276 B2 | 4/2009 | Froggatt et al. | |
| 7,527,594 B2 | 5/2009 | Vardi et al. | |
| 7,534,251 B2 | 5/2009 | WasDyke | |
| 7,535,797 B2 | 5/2009 | Peng et al. | |
| 7,547,304 B2 | 6/2009 | Johnson | |
| 7,564,949 B2 | 7/2009 | Sattler et al. | |
| 7,577,471 B2 | 8/2009 | Camus et al. | |
| 7,583,857 B2 | 9/2009 | Xu et al. | |
| 7,603,165 B2 | 10/2009 | Townsend et al. | |
| 7,612,773 B2 | 11/2009 | Magnin et al. | |
| 7,633,627 B2 | 12/2009 | Choma et al. | |
| 7,645,229 B2 | 1/2010 | Armstrong | |
| 7,658,715 B2 | 2/2010 | Park et al. | |
| 7,660,452 B2 | 2/2010 | Zwirn et al. | |
| 7,660,492 B2 | 2/2010 | Bates et al. | |
| 7,666,204 B2 | 2/2010 | Thornton et al. | |
| 7,672,790 B2 | 3/2010 | McGraw et al. | |
| 7,680,247 B2 | 3/2010 | Atzinger et al. | |
| 7,684,991 B2 | 3/2010 | Stohr et al. | |
| 7,711,413 B2 | 5/2010 | Feldman et al. | |
| 7,720,322 B2 | 5/2010 | Prisco | |
| 7,728,986 B2 | 6/2010 | Lasker et al. | |
| 7,734,009 B2 | 6/2010 | Brunner et al. | |
| 7,736,317 B2 | 6/2010 | Stephens et al. | |
| 7,742,795 B2 | 6/2010 | Stone et al. | |
| 7,743,189 B2 | 6/2010 | Brown et al. | |
| 7,762,954 B2 | 7/2010 | Nix et al. | |
| 7,766,896 B2 | 8/2010 | Kornkven Volk et al. | |
| 7,773,792 B2 | 8/2010 | Kimmel et al. | |

(56) References Cited

U.S. PATENT DOCUMENTS

| | | |
|---|---|---|
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 8,663,319 B2 * | 3/2014 | Ho .................. A61B 17/12036 623/2.11 |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0039445 A1 * | 11/2001 | Hall .................... A61F 2/2493 623/1.11 |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |

(56) References Cited

U.S. PATENT DOCUMENTS

| | | |
|---|---|---|
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0059412 A1 * | 3/2004 | Lytle, IV ............ A61F 2/2427 623/2.11 |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0163655 A1 * | 8/2004 | Gelfand ............ A61B 17/12036 128/898 |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0230219 A1 * | 11/2004 | Roucher, Jr. .......... A61M 25/04 606/194 |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |

(56) References Cited

U.S. PATENT DOCUMENTS

| | | |
|---|---|---|
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0030510 A1* | 1/2009 | Ho .................. A61B 17/12036 623/2.11 |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093801 A1* | 4/2009 | Crossman .......... A61B 18/1492 606/21 |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157577 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |

(56) References Cited

U.S. PATENT DOCUMENTS

| | | |
|---|---|---|
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |

(56) References Cited

FOREIGN PATENT DOCUMENTS

| | | |
|---|---|---|
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18 (17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12 (24):6033-6039.
Zitova et al., 2003, Image registration methods: A survey. Image and Vision Computing, 21(11):977-1000.
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).

(56) References Cited

OTHER PUBLICATIONS

International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.

(56) References Cited

OTHER PUBLICATIONS

Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87 (suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filed May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26 (1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.

Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.

(56) References Cited

OTHER PUBLICATIONS

Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, an euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61 (1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radiofrequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).

\* cited by examiner

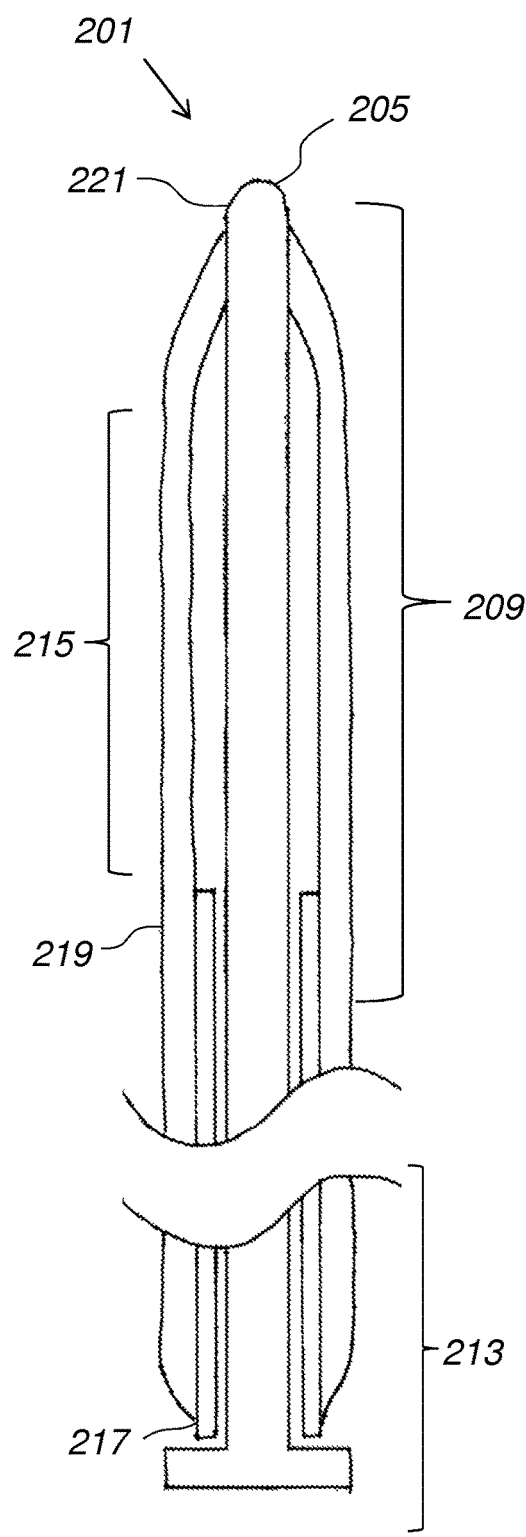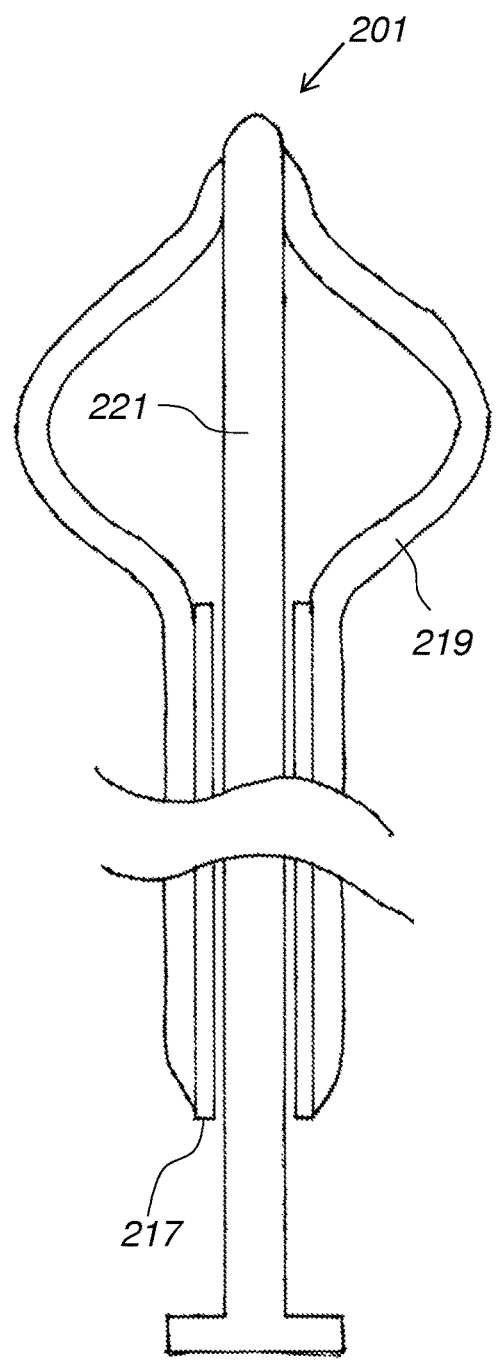
FIG. 3
FIG. 4

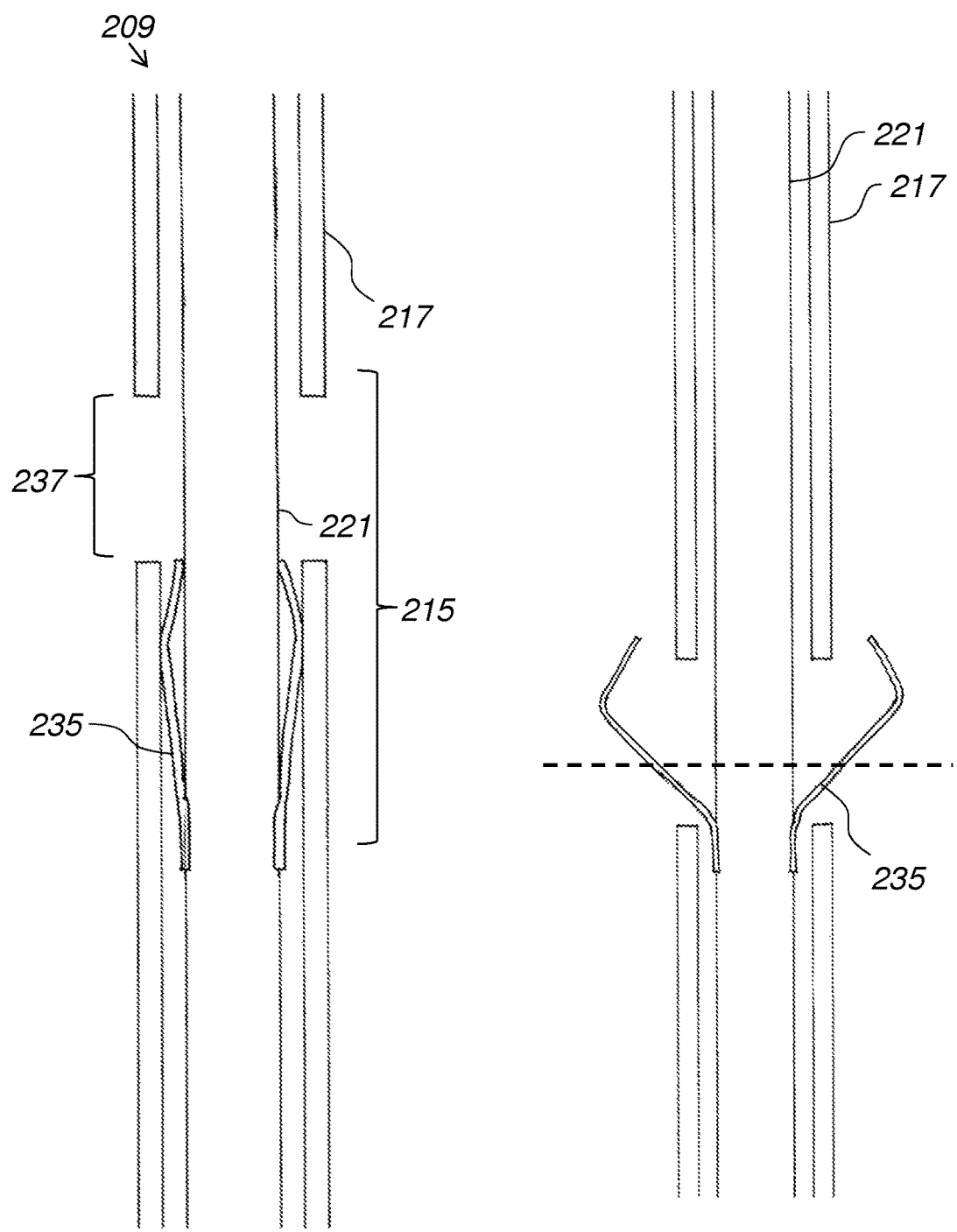

GUIDEWIRE WITH CENTERING MECHANISM

CROSS-REFERENCE TO RELATED APPLICATION

This application claims the benefit of, and priority to, U.S. Provisional Patent Application Ser. No. 61/774,228, filed Mar. 7, 2013, the contents of which are incorporated by reference.

FIELD OF THE INVENTION

The invention generally relates to a guidewire for intravascular intervention, and particularly to mechanisms for centering a guidewire within a vessel.

BACKGROUND

Some people are at risk of having a heart attack or stroke due to fatty plaque buildups in their arteries that restrict the flow of blood or even break off and block the flow of blood completely. Angioplasty is a procedure for treating sites that are affected by plaque. In this procedure, a needle is used to make an opening through a patient's skin and into a blood vessel, often the femoral artery in the patient's leg. A sheath is used to hold the opening open and a radiopaque dye is injected, allowing physician view the treatment site on x-ray and select a suitable balloon catheter and a guidewire for treatment.

The guidewire is then inserted through the hole and guided through the artery until the tip just passes the treatment site. The physician guides the wire by twisting and manipulating the proximal end that sits outside the patient. With the wire in place, the balloon catheter is slid over the proximal end and pushed forward until the balloon lies within the narrowed area. The balloon is then inflated to compress the plaque or to deliver a stent.

A number of problems are associated with this procedure. For example, in places where the guidewire lies against the side of the vessel, pushing the catheter over the guidewire can scrape the catheter against the vessel wall. The guidewire tends to be pushed against the vessel wall by any curve in the vessel. Specifically, the guidewire will push against the inside wall at the peak of the curve and against the outside wall at the ends of the curve.

Curves also present navigational challenges. For example, where a curve in the vessel lies close to a branch-point, it can be difficult to guide the tip of the wire into the correct branch due to the strong tendency of the curve to push the wire towards one side of the vessel.

Some positioning difficulties could be helped by an imaging guidewire. For example, a guidewire with an ultrasound imaging tip could help a physician navigate the vessels. However, the tendency of the guidewire to push up against the vessel wall interferes with imaging. If the imaging device is pushed into the vessel wall, it will not be useful for viewing its environment.

SUMMARY

The invention provides a guidewire with a mechanism for centering the guidewire within a vessel. A physician can operate the mechanism to cause it to lift the guidewire from the vessel walls and bias it towards the center of the vessel. Since the guidewire can be selectively lifted away from the vessel wall, scraping the catheter against the wall can be avoided, the tip can be guided into the correct branch of a bifurcation, and an imaging device can be used to its full potential. Thus the centering mechanism improves visibility and helps maneuver the guidewire to the location where fatty plaque is narrowing the arteries. The centering mechanism also minimizes trauma to healthy tissue by keeping the catheter from scraping through the vessel walls. Since the centering mechanism helps navigate the balloon to the affected site while protecting healthy tissue, angioplasty procedures can reach a number of sites that otherwise may have been inaccessible due to complex combinations of curves and branch-points within the blood vessels. Thus, by pushing the tip away from vessel walls and helping the physician orient the guidewire in the intended direction of travel, while also improving the view offered by imaging guidewires, a guidewire centering mechanism can be valuable for treating a person who is at serious risk for heart attack or stroke.

In certain aspects, the invention provides a guidewire for an intravascular procedure. The guidewire has an elongated shaft with a proximal portion and a distal portion comprising a distal tip. A centering mechanism is provided on the distal portion so that, when the distal portion is inserted into a vessel in a body, the centering mechanism can be operated to center the guidewire in the vessel. A guidewire can include a single centering mechanism, or a number of centering mechanisms disposed at different locations along the length.

In some embodiments, the centering mechanism uses a flexible sleeve that bows outward from an axis of the guidewire when compressed in a direction parallel to the axis. The flexible portion of the sleeve can be compressed by translating an outer sleeve along an inner core. For example, the proximal portion of the guidewire can present, to a physician, a graspable portion of the outer sleeve and of the inner core, allowing the physician to pull back the outer sleeve causing the centering mechanism to bow outwards. Moreover, the guidewire can be designed to transmit torque so that a physician can twist the proximal portion to cause the distal, inserted portion to twist. For example, torque can be transmitted by a key and keyway structure or a splined structure.

In certain embodiments, the centering mechanism includes a balloon. A balloon can be included that surrounds the guidewire and inflates into a torus. Or, a balloon can be included that inflates into a spheroid lobe on one side of the guidewire. Where a centering mechanism comprises one or a number (e.g., three) lobe-shaped balloons, one, selected ones, or all of the balloons can be inflated to center the guidewire without occluding the flow of blood. Other embodiments of a centering mechanism can be provided that do not occlude the flow of blood. For example, a centering mechanism can make use of one or more struts configured to expand out from the guidewire to push the wire away from the vessel wall. A sleeve or band can be included to constrain the strut or struts against a core member. Removing the sleeve from the vicinity of the strut results in the strut expanding away from the core member. Moreover, the centering mechanism can be configured so that the sleeve can be returned to its original position to compress the strut back against the core member.

A guidewire of the invention can include a centering mechanism along with other features. For example, a guidewire can include an imaging device. In some embodiments, an acoustic transducer is included for intravascular ultrasound imaging. The guidewire can be an IVUS imaging guidewire or can include an optoacoustic imaging fiber. An optoacoustic imaging fiber can use a photoacoustic transducer on an optical fiber that include one or more fiber Bragg grating to send an optical signal along the length of the fiber and guidewire while using an acoustical signal to image the tissue. The acoustic signal is received through the photoacoustic transducer and the signal information is carried out through the proximal end of the guidewire by the optical signal (e.g., as an interferometric signal).

In related aspects, the invention provides a coronary intervention system that uses a catheter with a treatment device and a guidewire that includes a centering mechanism. The guidewire is configured to be inserted into a blood vessel and the catheter is configured to slide over the guidewire to carry the treatment device to a treatment site. The catheter may itself include a structure for centering the guidewire in the vessel. This way, the guidewire may be centered by both the guidewire centering mechanism and the catheter structure, thus allowing the guidewire to be centered in more than once place, or giving a physician greater control of guidewire navigation. The guidewire centering mechanism can operate through the use of a balloon, one or more struts, or a pliable material configured to bow outwards from the guidewire. In certain embodiments, the guidewire has a central core member and an outer sleeve member that can be translated relative to the core member in a direction substantially parallel to an axis of the guidewire.

Aspects of the invention provide methods of performing angioplasty that include inserting a guidewire into a vessel of a patient and operating a centering mechanism disposed at a distal portion of the guidewire to bias the distal portion towards the center of the vessel. A catheter can be introduced to the treatment site by using the guidewire. These steps can be performed in any order. The guidewire centering mechanism can be employed when the catheter is already substantially advanced over the guidewire or the centering mechanism can be used when only the guidewire is substantially within the vessel, to aid in navigating the guidewire into position.

BRIEF DESCRIPTION OF THE DRAWINGS

FIG. 3 shows a centering mechanism for a guidewire.

FIG. 4 shows the centering mechanism of FIG. 3 in an expanded configuration.

FIG. 9 shows a strut-based embodiment of a centering mechanism.

FIG. 10 shows the mechanism of FIG. 9 in a deployed state.

DETAILED DESCRIPTION

Embodiments of the invention provide a guidewire with an expandable element that biases the guidewire to a particular location within a vessel, facilitating the precise placement of the guidewire and providing greater accuracy during subsequent catheter procedures. The expandable element can function as a centering mechanism, tending to center the guidewire within the vessel. A guidewire of the invention may also include detection elements that detect placement of the guidewire and subsequent therapy.

Figures 1, 2:
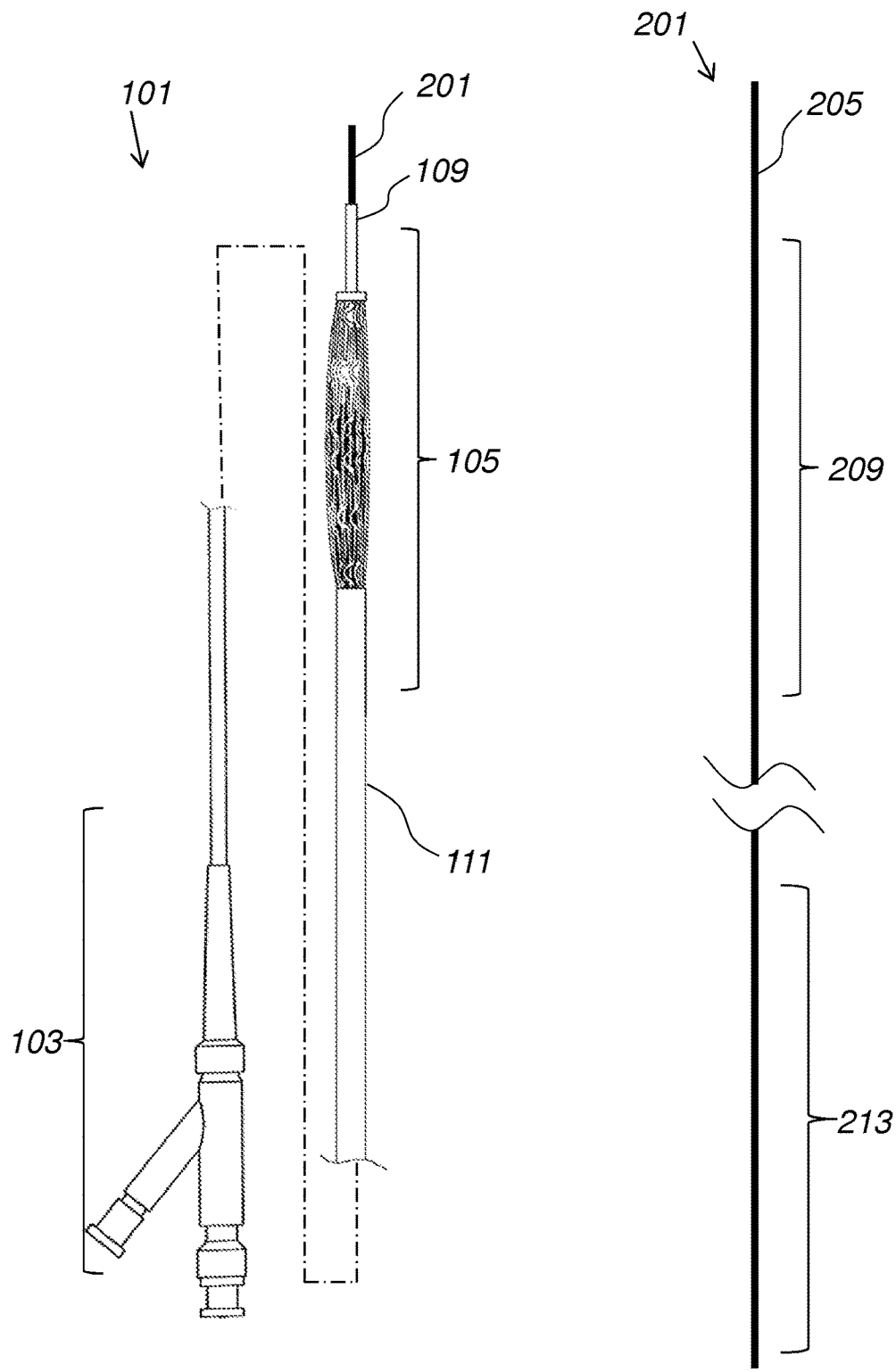
FIG. 1 shows a catheter according to certain embodiments of the invention.
FIG. 2 depicts guidewire for use with a catheter.

FIG. 1 shows a catheter 101 according to certain embodiments of the invention. Catheter 101 includes a proximal portion 103 that is generally outside of a patient during use and a distal portion 105 extending to a distal tip 109 configured for insertion into a patient. Distal portion 105 may generally include a treatment device. Guidewire 201 may be seen extending from distal tip 109. Pictured in FIG. 1 is a stent disposed around a balloon, but any suitable treatment device may be included. A length of catheter 101 extending through distal portion 105 generally defines a catheter shaft 111 capable of being delivered over guidewire 201. Intravascular balloon catheters are used for such procedures as balloon angioplasty, or percutaneous transluminal coronary angioplasty (PTCA). Catheter 101 generally includes a pliable material that provides flexibility or maneuverability, allowing catheter 101 to be guided to a treatment site in a patient's blood vessels. Preferably, catheter 101 has enough stiffness to allow it to be pushed to a target treatment site, and accordingly, an ability to optimize a balance of pliability versus stiffness or pushability is beneficial to medical use. Elongate shaft 111 may include any suitable material such as, for example, nylon, low density polyethylene, polyurethane, or polyethylene terephthalate (PET), or a combination thereof (e.g., layers or composites). Generally, shaft 111 will be capable of transmitting torque along an axis of the shaft. Catheter 101 may itself include a mechanism to aid in centering. For example, U.S. Pat. No. 7,547,304 to Johnson described a guidewire centering catheter tip. U.S. Pat. No. 5,660,180 to Malinowski describes an intravascular ultrasound imaging guidewire that can be centered through use of a catheter.

Catheter 101 may include an angioplasty balloon or other interventional device at distal portion 105 to expand or dilate blockages in blood vessels or to aid in the delivery of stents or other treatment devices. Blockages include the narrowing of the blood vessel called stenosis.

Typically, catheter shaft 111 will include a guidewire lumen so that the catheter may be advanced along guidewire 201. A guidewire lumen in a balloon catheter is described in U.S. Pat. No. 6,022,319. An inner surface of a guidewire lumen may include features such as a silicone resin or coating or a separate inner tube made, for example, of preformed polytetrafluoroethylene (PTFE). The PTFE tube may be installed within the catheter shaft by sliding it into place and then shrinking the catheter shaft around it. This inner PTFE sleeve provides good friction characteristics.

Other suitable materials for use in catheter 101 include high density polyethylene (HDPE) or combinations of material, for example, bonded in multiple layers.

Catheter 101 may include coaxial tubes defining separate inflation and guidewire lumens, for example, along a portion of, or an entirety of, a length of catheter 101. A plurality of lumens may be provided in parallel configuration or coaxial at one point and parallel at another, with a transition such as a plunging portion that traverses a wall located between the parallel and the coaxial portions (See, e.g., U.S. Pat. No. 7,044,964). Other possible configurations include one or more of a guidewire tube or guidewire lumen disposed outside of the balloon. Or the guidewire tube may be affixed to and extend along the wall of the balloon. Catheter 101 is generally introduced into vessel and advanced to a site of treatment by the use of guidewire 201.

FIG. 2 depicts guidewire 201. Guidewire 201 generally has a proximal portion 213 and a distal portion 209 terminating at distal tip 205. Guidewire 201 includes a mechanism to bias a location of guidewire 201 away from a vessel wall when guidewire 201 is inserted therein. Guidewires are discussed in U.S. Pat. Nos. 5,439,139 ;3,789,841; 6,059,738; and 6,423,012

FIG. 3 shows a centering mechanism 215 according to certain embodiments of the invention. Here, mechanism 215 includes a pliable polymer sheath 219 fixed to a core member 221 near a distal tip 205 of guidewire 201. The other end of sheath 219 is fixed to a sleeve member 217 disposed around core member 221. Sleeve member 217 is configured to translate longitudinally relative to core member 221, in a direction substantially parallel to an axis of guidewire 201.

FIG. 4 shows the centering mechanism 215 of FIG. 3 in an expanded configuration. When sleeve member 217 is translated in a direction towards distal tip 205, relative to core member 221, polymer sheath 219 bows outward from guidewire 201. Preferably, sheath 219 includes a polymer with elasticity, such as a urethane or PTFE polymer. An operator can center guidewire 201 by pushing sleeve 217 inwards towards a patient away from a proximal end of guidewire 201. If sheath 219 includes enough elasticity, it will tend to return to a non-expanded state of its own disposition. Sheath 219 can be substantially contiguous so that in its expanded state it tends to occlude blood flow. In other embodiments, sheath 219 can include slits parallel to an axis of guidewire 201 so that when it expands, separate strips of the polymer bow outwards and allow blood to flow past centering mechanism 215 even while deployed.

Figure 5:
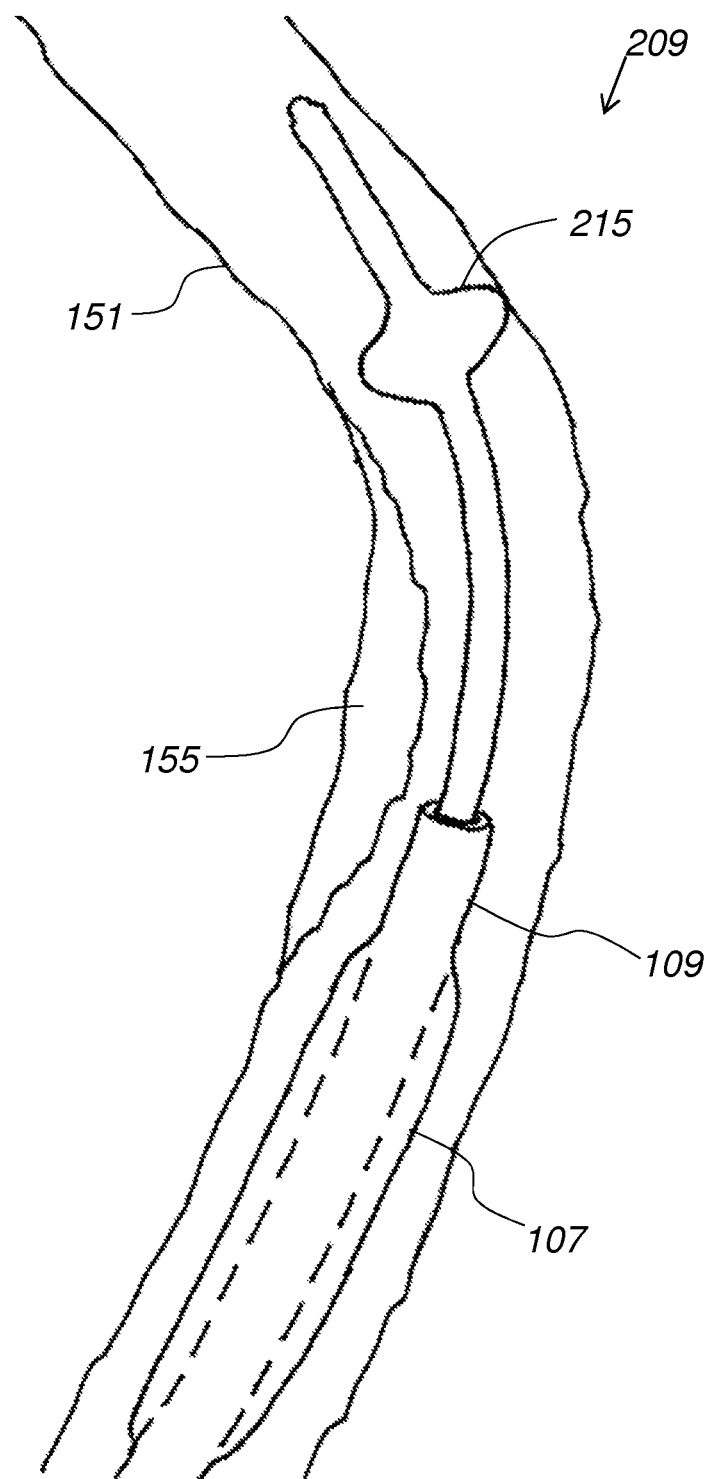
FIG. 5 shows a guidewire with centering mechanism being used in a vessel.

FIG. 5 shows centering mechanism 215 being deployed to center distal portion 209 of guidewire 201 near a treatment site 151. Here, distal tip 109 of catheter 101 is shown being used to introduce balloon 107. As can be seen in FIG. 5, distal tip 109 is kept away from the vessel walls to prevent damage to the tissue. An expandable pliable sheath is thus one mechanism for a centering mechanism. Other embodiments are provided.

Figure 6:
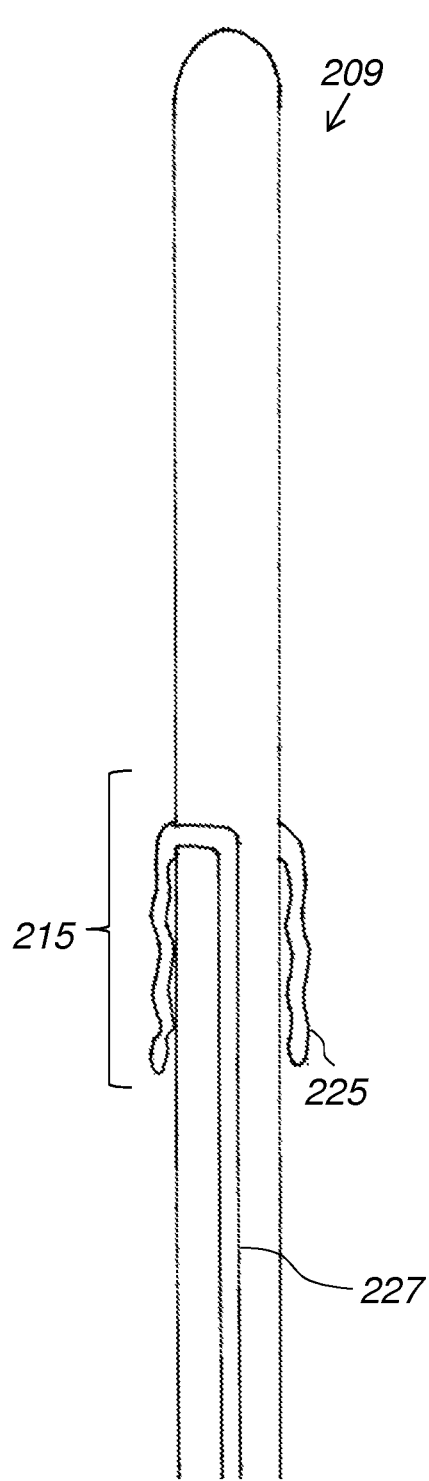
FIG. 6 illustrates an un-deployed balloon for use as a centering mechanism.
Figure 7:
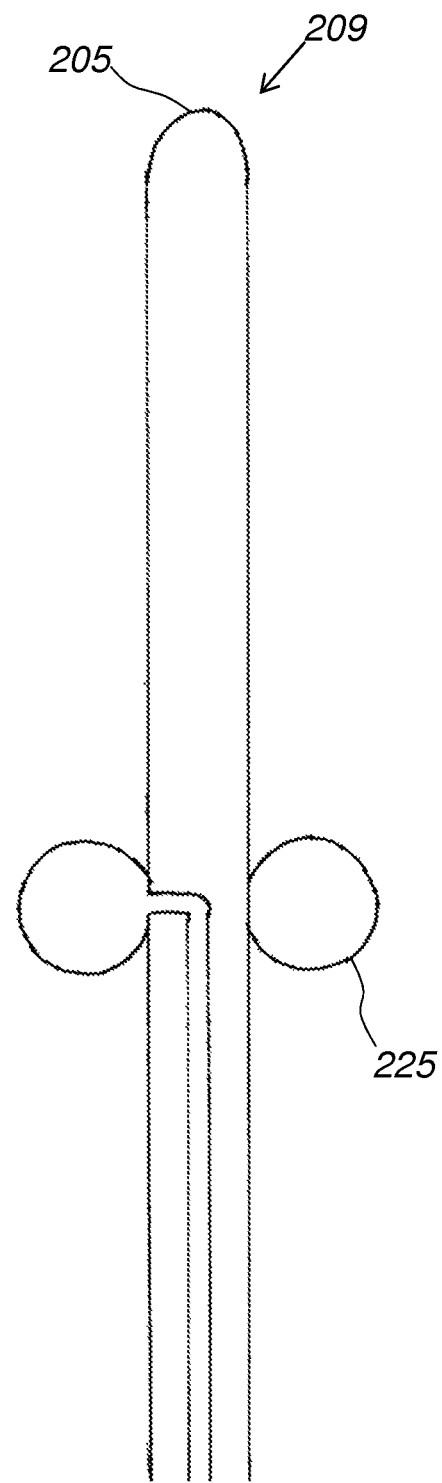
FIG. 7 shows a deployed balloon as a centering mechanism.
Figure 19:
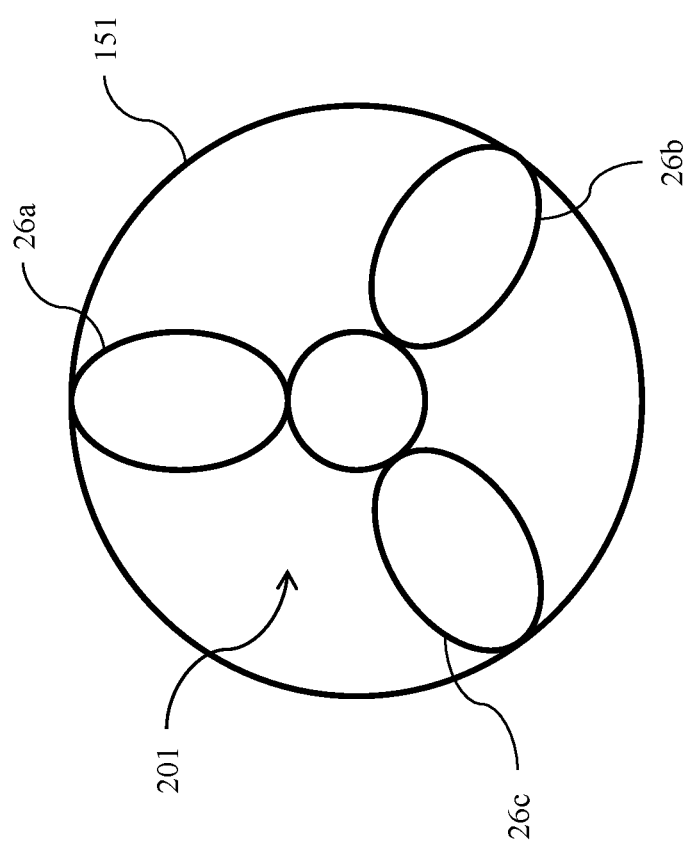
FIG. 19 shows a guidewire with centering mechanism being used in a vessel.

FIGS. 6 and 7 illustrate use of an inflatable balloon 225 at a distal portion 209 of guidewire 201 as a centering mechanism. Guidewire 201 includes balloon inflation lumen 227 (shown here disposed within guidewire 201—lumen 227 could also be provided as a tube along a side of guidewire 201). Forcing an inflation fluid (e.g., air, gas, water, saline, etc.) through inflation lumen inflates the balloon as shown in FIG. 7. FIG. 19 illustrates a guidewire 201 being centered within a vessel 151 with a plurality of balloons 26a, 26b, 26c as a centering mechanism.

Figure 8:
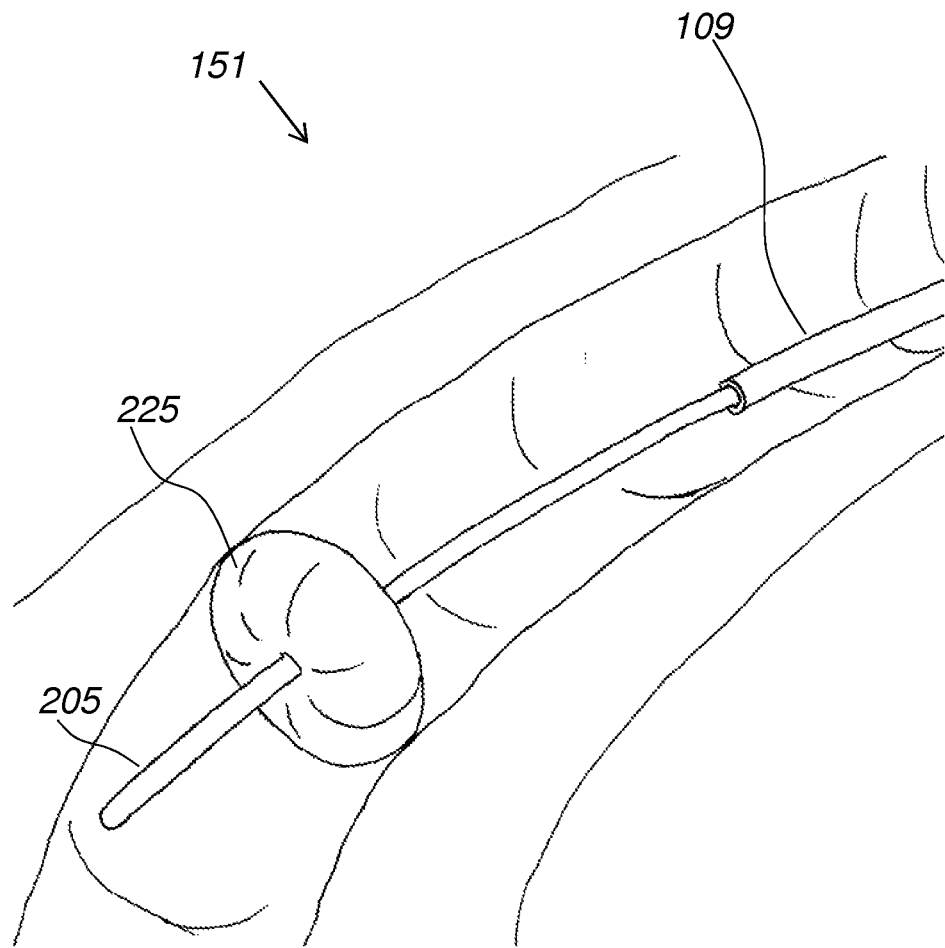
FIG. 8 shows use of balloon to center a guidewire at a site within a vessel.

FIG. 8 shows use of balloon 225 as centering mechanism 215 to center guidewire 201 in a site within a vessel 151. Distal tip of a catheter 109 is again illustrated to show that it is kept away from the vessel wall by centering mechanism 215.

FIG. 9 shows a strut-based embodiment of a centering mechanism 215 of the invention. Here, guidewire 201 includes a central core 221 surrounded by outer sleeve 217. Outer sleeve 217 compresses one or more of strut 235 against the side of core 221. Strut 235 can include a springy material or a shape-memory material (e.g., steel, iron, nitinol, etc.) that tends to bias strut 235 away from core 221. Sleeve 217 can include one or more aperture 237. When sleeve 217 is translated relative to core 221, aperture 237 is positioned over strut 235. Strut 235 is then released and expands away from core 221 under its own dispositional bias.

FIG. 10 shows centering mechanism 215 with struts 235 in a deployed state, expanded away from core 205.

Figures 11, 12:
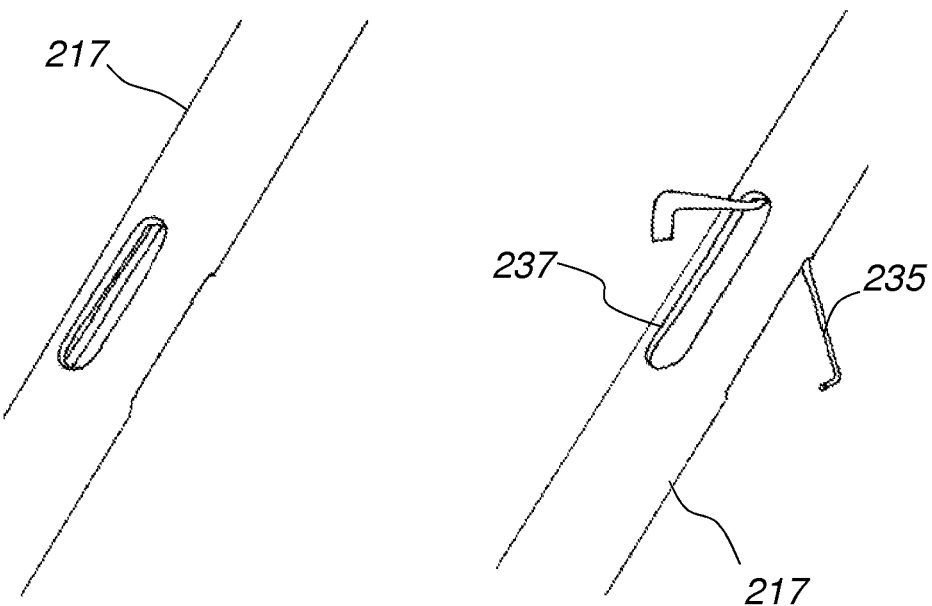
FIG. 11 gives a perspective view of an un-deployed strut-based centering mechanism.
FIG. 12 gives a perspective view of a deployed strut-based centering mechanism.

FIGS. 11 and 12 give perspective views of a centering mechanism 215 including a plurality of struts 235 in the compressed and expanded states, respectively. While shown here using a sleeve 217 with aperture 237, sleeve 217 could also operate to compress one or more of strut 235, and to allow them to expand, by having a terminal edge disposed in a vicinity of the strut or struts. Pull back on sleeve 217 can cause a terminal end of sleeve 217 to be removed from strut or struts 235, allowing them to expand. Sleeve 217 could then be pushed forward to compress strut or struts 235. Other arrangements are also possible and within the scope of the invention. For example, a terminus of sleeve 217 may have a straight (circular) edge, or may have a scalloped or slotted appearance, with individual recess for individual ones of strut 235.

Figure 13:
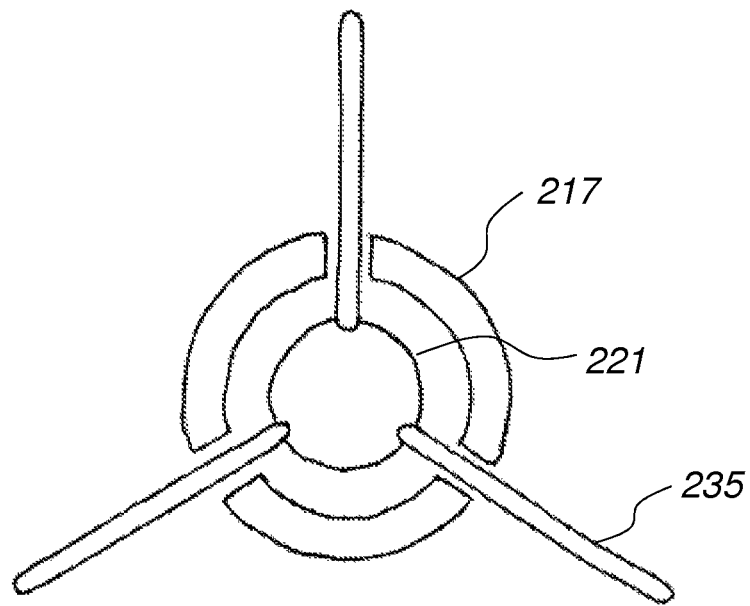
FIG. 13 is a cross-sectional view taken along the dotted line shown in FIG. 10.

FIG. 13 is a cross-sectional view of a centering mechanism 215 including a plurality of struts 235 taken along the dotted line shown in FIG. 10. While shown in FIG. 13 as including three of strut 235, centering mechanism 215 can include any number of strut 235. In fact, in certain embodiments, a single one of strut 235 provides a mechanism for biasing guidewire 201 away from a vessel wall in one direction.

Figure 14:
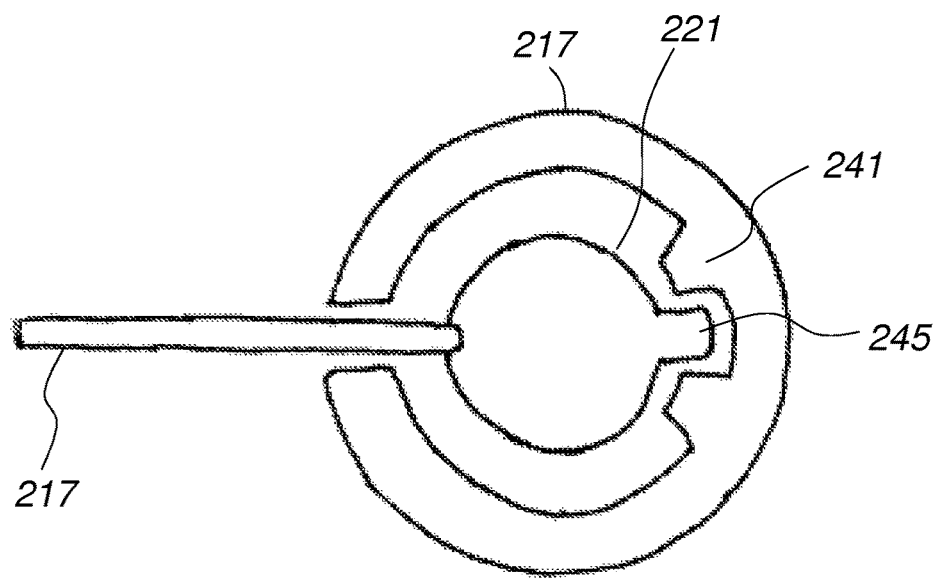
FIG. 14 shows a cross sectional view of a single strut for biasing guidewire.

FIG. 14 shows a cross sectional view of a single strut 235 for biasing guidewire 201 away from a vessel wall. Strut 235 as depicted in FIG. 14 may be operated substantially as described above with regards to FIGS. 9 and 10. Biasing a guidewire 201 away from a vessel wall may be particularly beneficial for a guidewire that is configured to transmit torque from one end to another. For example, an operator may view guidewire 201 via x-ray angiography and see that it needs to be pushed away from a vessel wall. The operator may twist the proximal end until the single strut 235 appears on the angiograph as oriented towards the wall. The operator may then deploy centering mechanism 215 to bias guidewire 201 towards a center of the vessel. Accordingly, embodiment of the invention that include a sheath surrounding a core can optionally include a structure for transmitting torque from one portion of guidewire 201 to another. Any suitable torque transmitting mechanism may be employed. In certain embodiments, torque is transmitted by a key and keyslot mechanism or by a spline mechanism.

As shown in FIG. 14, sleeve 217 includes bosses 241 defining a keyslot and core 221 includes a key 245 that fits therein. One of skill in the art will recognize that variations are possible such as placing one or more key or keyslot on either of core 221 and sleeve 217. Additionally or alternatively a surface of core 221, sleeve 217, or both can be splined.

Figure 15:
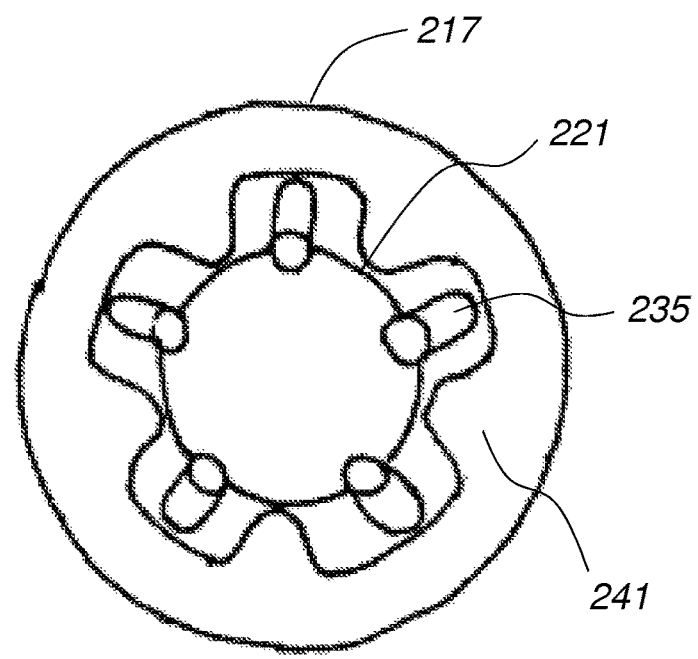
FIG. 15 shows a centering mechanism with five struts.

FIG. 15 shows a centering mechanism 215 for a guidewire 201 that includes five of strut 235. The centering mechanism 215 is depicted from the proximal perspective with each of strut 235 mounted to core 221 at a proximal end of strut 235. Thus a mounted, butt-end of each strut 235 is seen, with a elongated member of each strut extending away from the view, into the page, and biased away from core 221.

Struts 235 can be assembled on guidewire by any suitable means including, for example, welding, co-molding, clamping, banding, or adhesives. In some embodiments, a portion of strut 235 is swaged into the material of core 221. A band (e.g., metal or a polymer) may also be strapped around the bases of struts 235. Adhesives or spot welds may be additionally used, as desired. Thus a guidewire 201 of the invention includes a mechanism 215 for centering the guidewire within a vessel.

Figure 16:
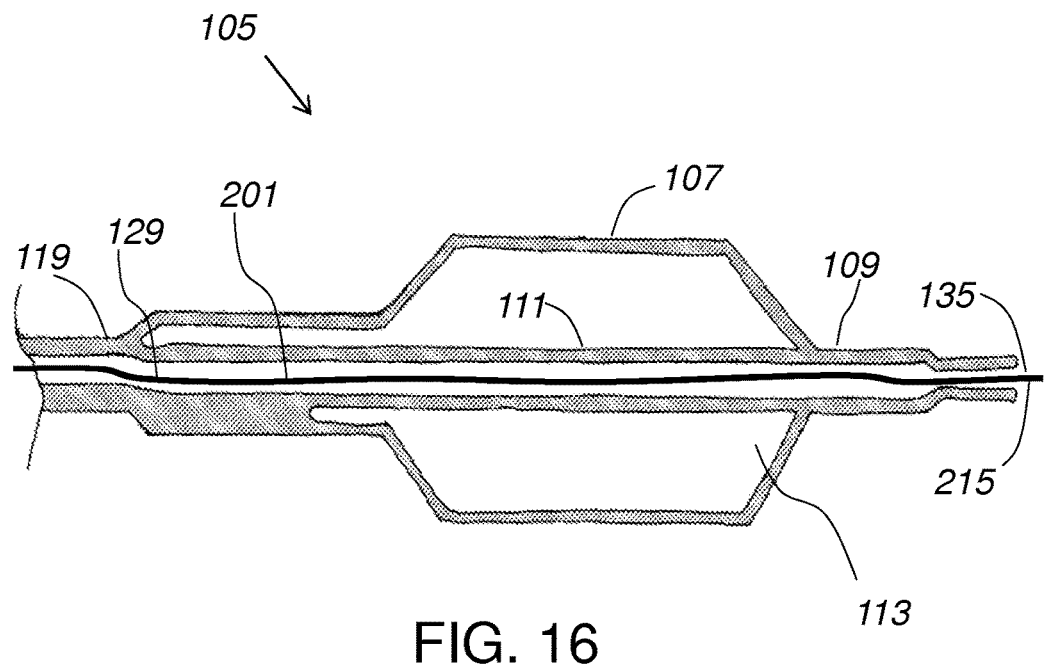
FIG. 16 shows a system including a guidewire and a balloon catheter.

FIG. 16 shows a cross-sectional view through distal portion 105 of catheter 101. Running through catheter 101 is catheter shaft 111 defining guidewire lumen 117 extending to distal tip 109. Inflation channel 119 may generally be disposed along guidewire lumen 117 along a length of catheter shaft 111. Balloon 107 surrounds inflation lumen 113 which is in fluid communication with inflation channel 119. Guidewire 201 may optionally include one or more of imaging device 135. Balloon 107 may be any suitable balloon known in the art such as, for example, an angioplasty balloon. Balloon 107 is configured to be expandable, and may be used to deliver stent 161 or to open an obstructed vessel. Balloon 107 generally includes a strong flexible material and exhibits a narrow profile in an un-inflated state. Any suitable material may be used for balloon 107 including, for example, polyolefins such as polyethylene, polyvinyl chloride, polyesters such as polyethylene terephthalate (PET) and polybutylene terephthalate (PBT) and copolyesters, polyether-polyester block copolymers, polyamides, polyurethane, poly(ether-block-amide) and the like. Balloons are described in U.S. Pat. No. 7,004,963; U.S. Pub. 2012/0071823; and U.S. Pub. 2008/0124495, the contents of each of which are incorporated by reference. Materials for balloon catheters are described in U.S. Pat. No. 5,820,594. Balloon catheters are described in U.S. Pat. Nos. 5,779,731 and 5,411,016.

In some embodiments, the balloon includes artificial muscle (electro-active polymer). Electro-active polymers exhibit an ability to change dimension in response to electric stimulation. The change may be driven by electric field E or by ions. Exemplary polymers that respond to electric fields include ferroelectric polymers (commonly known polyvinylidene fluoride and nylon 11, for example), dielectric EAPs, electro-restrictive polymers such as the electro-restrictive graft elastomers and electro-viscoelastic elastomers, and liquid crystal elastomer composite materials. Ion responsive polymers include ionic polymer gels, ionomeric polymer-metal composites, conductive polymers and carbon nanotube composites. Common polymer materials such as polyethylene, polystyrene, polypropylene, etc., can be made conductive by including conductive fillers to the polymer to create current-carrying paths. Many such polymers are thermoplastic, but thermosetting materials such as epoxies, may also be employed. Suitable conductive fillers include metals and carbon, e.g., in the form of sputter coatings. Electroactive polymers are discussed in U.S. Pat. Nos. 7,951,186; 7,777,399; and U.S. Pub. 2007/0247033, the contents of each of which are incorporated by reference.

In some embodiments, guidewire 201 includes imaging fiber 129 extending from a proximal portion 103 of catheter 101. At proximal portion 103, imaging fiber 129 may be operably coupled to a control unit (not pictured) via an optical coupler. Imaging device 135 may include any suitable imaging technology known in the art. In certain embodiments, device 101 uses optical-acoustic transduction to perform ultrasound imaging using imaging fiber 129 and imaging device 135.

Figure 17:
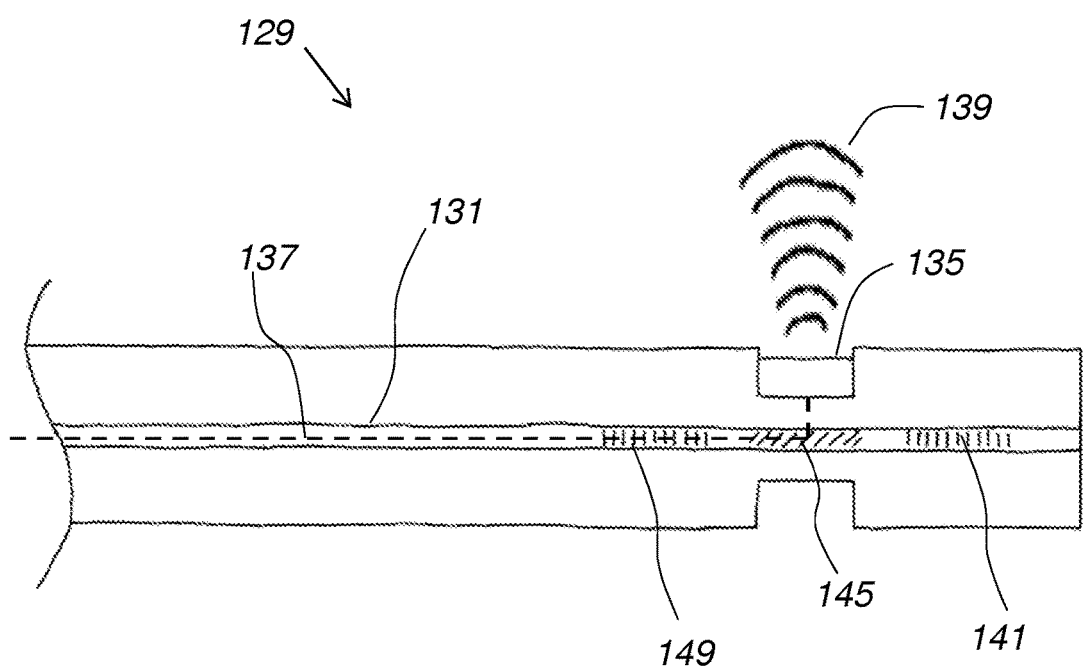
FIG. 17 shows an imaging fiber for use on a guidewire of the invention.

FIG. 17 shows an imaging fiber 129 configured for optical-acoustic imaging. Along fiber 129, a cladding surrounds fiber core 131. Light 137 is transmitted from the control unit down a length of fiber 129. Within fiber core, fiber Bragg grating 149 partially reflects light 137. Also, where included, terminal fiber Bragg grating 141 reflects light. Additionally, blazed fiber Bragg grating 145 reflects light in a direction substantially radial to an axis of fiber 129. The radial portion of the path of light 137 extends to photoacoustic transducer 135. When light 137 impinges on photoacoustic transducer 135, phonons are generated, leading to thermal strain of photoacoustic transducer 135. Thus, photoacoustic transducer 135 uses incoming light 137 as an energy source to generate a longitudinal pressure wave 139. When distal portion 105 is in a patient's vessel, pressure wave 139 can be used for ultrasonic imaging of material in the vessel, plaque, the vessel wall, surrounding tissue, other material, or a combination thereof. Parts of wave 139 that bounce back constitute the return signal that will contribute to the ultrasonic image data. Imaging fibers and methods of making them are discussed in U.S. Pat. No. 8,059,923, the contents of which are incorporated by reference for all purposes.

In some embodiments, this return signal impinges on photoacoustic transducer 135. The energy of return signal causes a vibration or deformation of photoacoustic transducer 135. This results in a change in length of light path 137. In some embodiments, the primary change in length of light path 137 is in the radial portion extending between photoacoustic transducer 135 and fiber core 131, substantially perpendicular to an axis of fiber 129. However, deformations in geometry of cladding 133 may result in a change of length of light path 137 in, for example, the region between fiber Bragg grating 149 and blazed fiber Bragg grating 145. Depending on a desired embodiment, one may be favored over the other by cladding a portion of fiber 129 in a material with different rigidity or changing proportions of the depicted elements. Light reflected by blazed fiber Bragg grating from photoacoustic transducer 135 and into fiber core 131 combines with light that is reflected by either fiber Bragg grating 149 or 141 (either or both may be including in various embodiments). The light from photoacoustic transducer 135 will interfere with light reflected by either fiber Bragg grating 149 or 141 and the light 137 returning to the control unit will exhibit an interference pattern. This interference pattern encodes the ultrasonic image captured by imaging device 135. The light 137 can be received into photodiodes within a control unit and the interference pattern thus converted into an analog electric signal. This signal can then be digitized using known digital acquisition technologies and processed, stored, or displayed as an image of the target treatment site. An incoming optical acoustical signal impinging on diodes creates an analog electrical signal which can be digitized according to known methods. Methods of digitizing an imaging signal are discussed in Smith, 1997, THE SCIENTIST AND ENGINEER'S GUIDE TO DIGITAL SIGNAL PROCESSING, California Technical Publishing (San Diego, Calif.), 626 pages; U.S. Pat. Nos. 8,052,605;

6,152,878; 6,152,877; 6,095,976; U.S. Pub. 2012/0130247; and U.S. Pub. 2010/0234736, the contents of each of which are incorporated by reference for all purposes.

In related embodiments, imaging fiber 129 operates without a blazed fiber Bragg grating and detects a change in path length between fiber Bragg gratings 149 and 141 associated by a strain induced on fiber 129 by the impinging sonic return signal. In some embodiments, separate imaging fibers 129 are used to send and to receive an ultrasonic image. Methods of optic-acoustic imaging using fiber Bragg gratings for use with the invention are discussed in U.S. Pat. No. 8,059,923 and U.S. Pub. 2008/0119739, the contents of which are incorporated by reference in their entirety.

The invention includes methods of providing an array of imaging fibers 129 that can be disposed around guidewire 201 and further provides methods of creating a plurality of image detectors 135 that are all oriented in a desired direction. In some embodiments, a plurality of substantially featureless optical fibers are arrayed in a sheet substantially parallel to one another. The sheet of fibers may be positioned on a sheet of material that may optionally have an adhesive on the surface. Additionally or alternatively, a cementing material may be applied to the sheet-like array of fibers. The fibers 129 may be arrayed in substantially straight lines (e.g., by combing prior to application of adhesive or cement) or may be in other conformations. For example, introducing a wavy or zigzag pattern into a portion of the fibers 129 may give them slack, or "play", that allows image detectors to stay in place as guidewire 201 bends or twists. Once the fibers are so arrayed and held in place, the fiber Bragg gratings may then be formed in all of them. The fiber Bragg gratings may be formed by an inscribing method using a UV laser and may be positioned through the use of interference or masking. Inscribing and use of fiber Bragg gratings are discussed in Kashyap, 1999, FIBER BRAGG GRATINGS, Academic Press (San Diego, Calif.) 458 pages; Othonos, 1999, FIBER BRAGG GRATINGS: FUNDAMENTALS AND APPLICATIONS IN TELECOMMUNICATIONS AND SENSING, Artech (Norwood, Mass.) 433 pages; U.S. Pat. Nos. 8,301,000; 7,952,719; 7,660,492; 7,171,078; 6,832,024; 6,701,044; U.S. Pub. 2012/0238869; and U.S. Pub. 2002/0069676, the contents of each of which are incorporated by reference.

Detectors 135 can then be introduced by grinding a channel into the surface of all of the fibers. If done with the fibers un-cemented, the fibers can be rolled over and the grinding continued so that each fiber has an annular channel extending around the fiber. Fiber Bragg grating 149, 141, both, others, or a combination thereof can be formed, as well as any desired number of blazed fiber Bragg grating 145 in each fiber 129 (see FIG. 17). A channel or cutaway can be formed for image detector and may optionally be filled with a photoacoustic transducer material. Suitable photoacoustic materials can be provided by polydimethylsiloxane (PDMS) materials such as PDMS materials that include carbon black or toluene. Imaging fibers and methods of making them are discussed in U.S. Pat. No. 8,059,923, the contents of which are incorporated by reference for all purposes. Once the sheet-like array is bound together (e.g., the adhesive has set), the sheet can be applied to a surface—for example, wrapped around catheter shaft 111.

Other imaging modalities may be included in system 101. Imaging device 135 can employ any suitable imaging modality known in the art. Suitable imaging modalities include intravascular ultrasound (IVUS), optical coherence tomography (OCT), optical-acoustical imaging, and others. For ultrasound imaging, catheter 101 may include an ultrasound transducer as imaging device 135. Ultrasonic imaging catheters are discussed in U.S. Pat. No. 5,054,492 to Scribner; U.S. Pat. No. 5,024,234 to Leary; and U.S. Pat. No. 4,841,977 to Griffith. Systems for IVUS are discussed in U.S. Pat. No. 5,771,895; U.S. Pub. 2009/0284332; U.S. Pub. 2009/0195514 A1; U.S. Pub. 2007/0232933; and U.S. Pub. 2005/0249391, the contents of each of which are hereby incorporated by reference in their entirety. OCT systems and methods are described in U.S. Pub. 2011/0152771; U.S. Pub. 2010/0220334; U.S. Pub. 2009/0043191; U.S. Pub. 2008/0291463; and U.S. Pub. 2008/0180683, the contents of each of which are hereby incorporated by reference in their entirety. In certain embodiments, catheter 101 makes use of a combination of optical and acoustic signal propagation for imaging capabilities.

Figure 18:
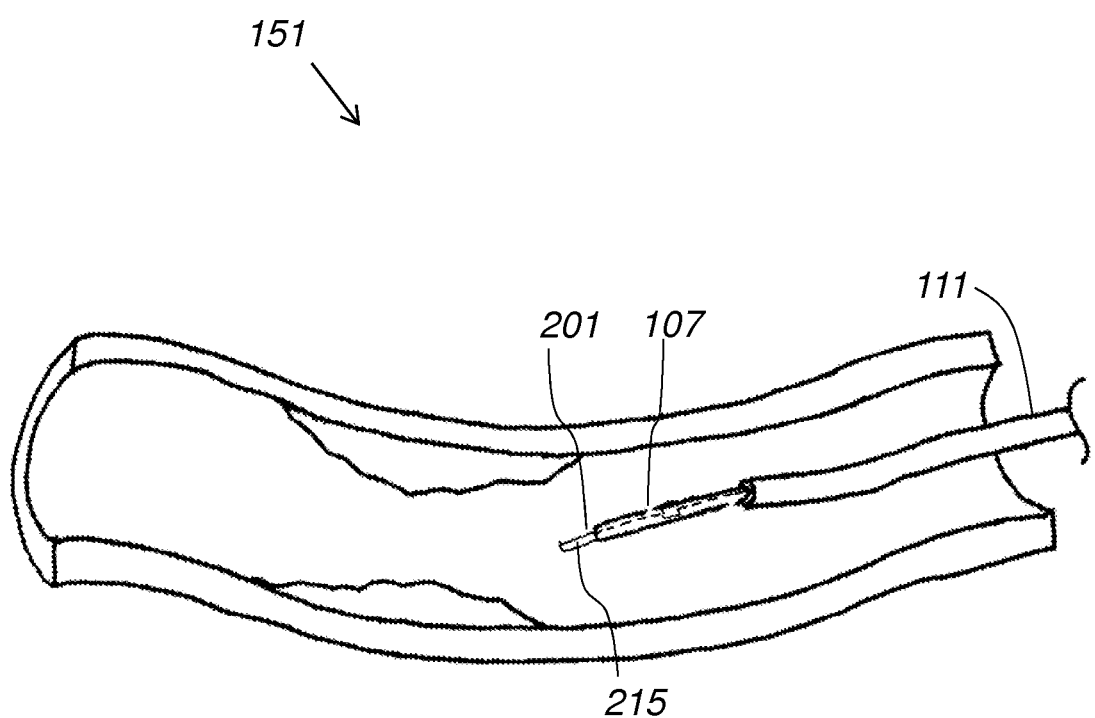
FIG. 18 illustrates a guidewire being introduced into a vessel.

FIG. 18 illustrates a guidewire 201 with centering mechanism 215 being introduced into a treatment site 151 of a vessel so that catheter body 111 can be used to deliver balloon 107 to the treatment site. As shown in FIG. 18, as catheter 101 approaches treatment site 151 (such as a region of a blood vessel affected by atherosclerotic plaque), a physician can view site 151 on a monitor of an associated medical imaging instrument (not pictured). Using, for example, IVUS or optical-acoustic imaging, the vessel wall is viewed to monitor for the location of atherosclerotic plaques. Monitoring a position of catheter 111 may also be optionally combined with use of standard x-ray angiographic techniques. When balloon 107 is positioned at the target treatment site, it is inflated to open a passageway that will allow blood to flow past the stenosized (narrowed) portion of the vessel after the balloon is deflated. Balloon 107 may also be optionally used to deploy a stent. Such vascular intervention procedures by catheter are often performed in specialized clinical environments known as cath labs. Cath labs and associated imaging instrumentation (e.g., IVUS and OCT instruments) are known in the art. For example, IVUS is discussed in U.S. Pat. Nos. 8,289,284; 7,773,792; U.S. Pub. 2012/0271170; U.S. Pub. 2012/0265077; U.S. Pub. 2012/0226153; and U.S. Pub. 2012/0220865. Optical-acoustic imaging structures (e.g., for imaging fiber 129) are discussed in U.S. Pat. Nos. 8,059,923; 7,660,492; 7,527,594; 6,261,246; 5,997,523; U.S. Pub. 2012/0271170 and U.S. Pub. 2008/0119739. The contents of each of these patents and publications are incorporated by reference in their entirety for all of their teachings and for all purposes. As shown in FIG. 8, use of a centering mechanism 215 allows for centering of guidewire 201 in the vessel, thus preventing balloon 107 or another portion of catheter 101 from scraping the vessel wall.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A guidewire for an intravascular procedure, the guidewire comprising:
   an elongated shaft with a proximal portion and a distal portion comprising a closed distal tip, wherein the distal portion is configured to be inserted into a vessel in a body; and
   a centering mechanism at the distal portion operable to bias a portion of the guidewire towards the center of the vessel, the centering mechanism comprising a structure that can be expanded away from or contracted towards the guidewire;
   wherein the centering mechanism does not occlude blood flow through the vessel;
   wherein the centering mechanism comprises a plurality of balloons that each inflate into a spheroid shape; and
   wherein the guidewire is sized and shaped to extend through a lumen of a catheter such that the catheter is configured to move within the vessel over the guidewire.

2. The guidewire of claim 1, further comprising an imaging device.

3. The guidewire of claim 1, wherein the vessel is an artery or vein.

4. The guidewire of claim 1, wherein the closed distal tip is spaced from the centering mechanism.

5. A coronary intervention system comprising:
   a catheter comprising a treatment device; and
   a guidewire comprising a closed distal tip and a centering mechanism, the centering mechanism comprising a structure that can be expanded away from or contracted towards the guidewire, wherein the centering mechanism does not occlude blood flow through a blood vessel, wherein the centering mechanism comprises a plurality of balloons that each inflate into a spheroid shape, and
   wherein the guidewire is configured to be inserted into the blood vessel and the catheter is configured to be slid over the guidewire to carry the treatment device to a treatment site.

6. The system of claim 5, wherein the centering mechanism is disposed at a distal portion of the guidewire and operable to bias the distal portion of the guidewire towards the center of the vessel.

7. The system of claim 5, wherein the treatment device comprises a stent.

8. A method of performing angioplasty, the method comprising:
   inserting a guidewire into a vessel of a patient, the guidewire comprising a proximal portion and a distal portion, wherein the distal portion comprises a closed distal tip;
   operating a centering mechanism disposed at the distal portion to bias the distal portion towards the center of the vessel, wherein the centering mechanism does not occlude blood flow through a blood vessel, and wherein the centering mechanism comprises a plurality of balloons that each inflate into a spheroid shape; and
   using the guidewire to introduce a catheter into a treatment site within the vessel, wherein the catheter is advanced over the guidewire into the treatment site.

9. The method of claim 8, wherein the catheter is introduced prior to operating the centering mechanism.

* * * * *